(12) United States Patent
Meena et al.

(10) Patent No.: US 12,175,677 B2
(45) Date of Patent: Dec. 24, 2024

(54) SYSTEM AND A METHOD FOR ANALYSING A FLUID SAMPLE

(71) Applicant: Neodocs Healthcare PVT. LTD., Mumbai (IN)

(72) Inventors: Anurag Meena, Mumbai (IN); Pratik Lodha, Mumbai (IN); Nikunj Malpani, Mumbai (IN)

(73) Assignee: Neodocs Healthcare PVT. LTD., Mumbai (IN)

( * ) Notice: Subject to any disclaimer, the term of this patent is extended or adjusted under 35 U.S.C. 154(b) by 0 days.

(21) Appl. No.: 18/620,425

(22) Filed: Mar. 28, 2024

(65) Prior Publication Data

US 2024/0338827 A1   Oct. 10, 2024

Related U.S. Application Data

(63) Continuation of application No. PCT/IN2024/050250, filed on Mar. 11, 2024.

(30) Foreign Application Priority Data

Apr. 10, 2023   (IN) .............................. 202321026673

(51) Int. Cl.
*G06T 7/00* (2017.01)
*G06K 7/14* (2006.01)
(Continued)

(52) U.S. Cl.
CPC .......... *G06T 7/0014* (2013.01); *G06K 7/1417* (2013.01); *G06T 7/90* (2017.01);
(Continued)

(58) Field of Classification Search
CPC .......... G01N 2021/7759; G01N 21/78; G01N 21/8483; G01N 33/52; G06T 7/90;
(Continued)

(56) References Cited

U.S. PATENT DOCUMENTS 11,506,656 B2 * 11/2022 Harris .................. G06T 7/0014
2016/0252460 A1   9/2016 Burg et al.
(Continued)

OTHER PUBLICATIONS

Ko, Jina, et al. "Machine learning to detect signatures of disease in liquid biopsies—a user's guide." Lab on a Chip 18.3 (2018): 395-405. (Year: 2018).*
Mercan, Ö. B., Kiliç, V., & Şen, M. (2021). Machine learning-based colorimetric determination of glucose in artificial saliva with different reagents using a smartphone coupled uPAD. Sensors and Actuators B: Chemical, 329, 129037. (Year: 2021).*

*Primary Examiner* — Li Liu
(74) *Attorney, Agent, or Firm* — Shumaker, Loop & Kendrick, LLP (57) ABSTRACT

A system and a method for analysing a fluid sample. The system receives an image of a test strip. The system identifies a set of regions in the image. The set of regions comprises a code, a set of position markers, a set of colour markers, and a set of chemical pads. Subsequently, the system obtains test data based on the code. The test data includes a set of health parameters, and chemical pad data. Further, the system determines a degree of chemical reaction by analysing the set of chemical pads based on the test data. Furthermore, the set of health parameters may be computed based on the extent of the chemical reaction.

18 Claims, 8 Drawing Sheets

(51) Int. Cl.
*G06T 7/90* (2017.01)
*G16H 15/00* (2018.01)

(52) U.S. Cl.
CPC .................... *G16H 15/00* (2018.01); *G06T 2207/10024* (2013.01); *G06T 2207/20081* (2013.01); *G06T 2207/30004* (2013.01)

(58) Field of Classification Search
CPC ............. G06T 7/0012; G06T 7/0014; G06T 15/506; G06V 10/82; G06V 10/60; G06V 10/56; G06N 20/00
See application file for complete search history.

(56) References Cited

U.S. PATENT DOCUMENTS

| | | | |
|---|---|---|---|
| 2016/0370389 A1* | 12/2016 | Barstis | G01N 21/8483 |
| 2019/0346429 A1* | 11/2019 | Harris | G01N 21/78 |
| 2020/0126227 A1* | 4/2020 | Adiri | G06V 10/82 |
| 2020/0191722 A1* | 6/2020 | Lu | G01N 21/80 |
| 2021/0158556 A1* | 5/2021 | Wu | G06T 7/73 |
| 2021/0255110 A1* | 8/2021 | Beck | G01N 33/84 |
| 2021/0295515 A1* | 9/2021 | Berg | G06T 7/11 |
| 2022/0254133 A1* | 8/2022 | Adsul | G06V 10/225 |
| 2022/0291205 A1 | 9/2022 | Heron et al. | |
| 2023/0289930 A1* | 9/2023 | Vyas | G06T 17/20 |

\* cited by examiner

SYSTEM AND A METHOD FOR ANALYSING A FLUID SAMPLE

PRIORITY INFORMATION

The present application is a Continuation of and claims priority from PCT Application Number PCT/IN2024/050250, filed on Mar. 11, 2024, which in turn takes priority from Indian Patent Application Number 202321026673, filed on Apr. 10, 2023.

TECHNICAL FIELD

The present subject matter described herein, in general, relates to the field of image processing for medical purposes. More specifically, the present disclosure relates to systems and methods for analysing a fluid sample.

BACKGROUND

Urine testing is a common diagnostic tool used to evaluate various aspects of health, such as kidney function, liver function, and the presence of infections or other medical conditions. Typically, urine samples are analysed using test strips that detect the presence of specific substances or biomarkers in the urine. However, traditional urine testing methods involve manual interpretation of test strip colours, which may be subjective and prone to human error. Furthermore, manual interpretation is time-consuming and may not be practical in high-throughput clinical settings.

Computer vision has been used to collect quantitative and qualitative clinical data in medical testing. Conventionally, regulatory agencies-approved clinical devices include specialised hardware, such as pre-calibrated scanners that work under controlled capture and lighting circumstances. In addition, these devices have classifiers that operate based on the calibrated pictures generated by the scanners.

Smartphones now feature tremendous computing power, wireless Internet connection, and high-resolution cameras. Smartphones as regulatory-approved clinical devices are difficult for three key reasons. First, smartphone camera quality may vary owing to brand and model differences in settings and image. Even within a model, photos may vary. Second, smartphone findings may differ in non-uniformly illuminated situations. Thirdly, non-medical smartphone users may struggle to follow precise protocols. The present embodiments provide new and improved methods for using personal communication devices for medical testing.

SUMMARY

Before the present system(s) and method(s), are described, it is to be understood that this application is not limited to the particular system(s), and methodologies described, as there can be multiple possible embodiments that are not expressly illustrated in the present disclosures. It is also to be understood that the terminology used in the description is for the purpose of describing the particular implementations or versions or embodiments only and is not intended to limit the scope of the present application. This summary is provided to introduce aspects related to a system and a method for analysing a fluid sample. This summary is not intended to identify essential features of the claimed subject matter, nor is it intended for use in determining or limiting the scope of the claimed subject matter.

In one implementation, a method for analysing a fluid sample is disclosed. The method comprises receiving an image of a test strip. It may be noted that a part of the test strip is dipped in a fluid sample. Further, a set of regions in the image may be identified. The set of regions comprises a code, a set of position markers, a set of colour markers, and a set of chemical pads. Subsequently, test data may be obtained based on the code. The test data comprises a set of health parameters, and chemical pad data. Further, a degree of chemical reaction may be determined by analysing the set of chemical pads based on the test data. The set of chemical pads is analysed using a reaction model. Further, the set of health parameters may be computed based on the extent of the chemical reaction. The set of health parameters is computed using a test model. In one aspect, the aforementioned method for analysing a fluid sample may be performed by a processor using programmed instructions stored in a memory.

In another implementation, a non-transitory computer program product having embodied thereon a computer program for analysing a fluid sample is disclosed. The computer program product storing instructions for receiving an image of a test strip. It may be noted that a part of the test strip is dipped in a fluid sample. Further, the program may comprise a program code for identifying a set of regions in the image. The set of regions comprises a code, a set of position markers, a set of colour markers, and a set of chemical pads. Subsequently, the program may comprise a program code for obtaining test data based on the code. The test data comprises a set of health parameters, and chemical pad data. Further, the program may comprise a program code for determining a degree of chemical reaction by analysing the set of chemical pads based on the test data. The set of chemical pads is analysed using a reaction model. Further, the program may comprise a program code for computing the set of health parameters based on the extent of the chemical reaction. The set of health parameters is computed using a test model.

BRIEF DESCRIPTION OF THE DRAWINGS

The foregoing detailed description of embodiments is better understood when read in conjunction with the appended drawings. For the purpose of illustrating the present subject matter, an example of a construction of the present subject matter is provided as figures, however, the invention is not limited to the specific method and system for analysing a fluid sample disclosed in the document and the figures.

The present subject matter is described in detail with reference to the accompanying figures. In the figures, the left-most digit(s) of a reference number identifies the figure in which the reference number first appears. The same numbers are used throughout the drawings to refer to various features of the present subject matter.

The figure depicts an embodiment of the present disclosure for purposes of illustration only. One skilled in the art will readily recognize from the following discussion that alternative embodiments of the structures and methods illustrated herein may be employed without departing from the principles of the disclosure described herein.

DETAILED DESCRIPTION

Some embodiments of this disclosure, illustrating all its features, will now be discussed in detail. The words "receiving," "identifying," "obtaining," "determining," "computing," and other forms thereof, are intended to be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise. Although any system and methods similar or equivalent to those described herein can be used in the practice or testing of embodiments of the present disclosure, the exemplary, system and methods are now described.

The disclosed embodiments are merely examples of the disclosure, which may be embodied in various forms. Various modifications to the embodiment will be readily apparent to those skilled in the art, and the generic principles herein may be applied to other embodiments. However, one of ordinary skill in the art will readily recognize that the present disclosure is not intended to be limited to the embodiments described but is to be accorded the widest scope consistent with the principles and features described herein.

The present subject matter discloses a method and a system for analysing a fluid sample based on an image of a test strip. The system may receive an image of a test strip that has been dipped in a fluid sample. In an example, the fluid sample may be a urine sample. Further, the system identifies a set of regions in the image. The set of regions may comprise a code, a set of position markers, a set of colour markers, and a set of chemical pads.

The system further fetches test data based on the code present on the image of the test strip. The test data comprises a set of health parameters and chemical pad data. Furthermore, a degree of chemical reaction is determined by analysing the image, specifically the set of chemical pads present on the image of the test strip, based on the test data. Finally, the set of health parameters is computed based on the extent of the chemical reaction using a test model.

The disclosed method provides an automated and objective approach to fluid sample analysis, reducing the potential for subjective human error. Furthermore, the use of image processing techniques enables the method to be performed using a device, such as a smartphone, a tablet, or any electronic device having a camera and internet connectivity, which can be used to capture and analyse the image of the test strip. This makes the method more accessible and convenient for users, particularly in low-resource settings.

Figure 1:
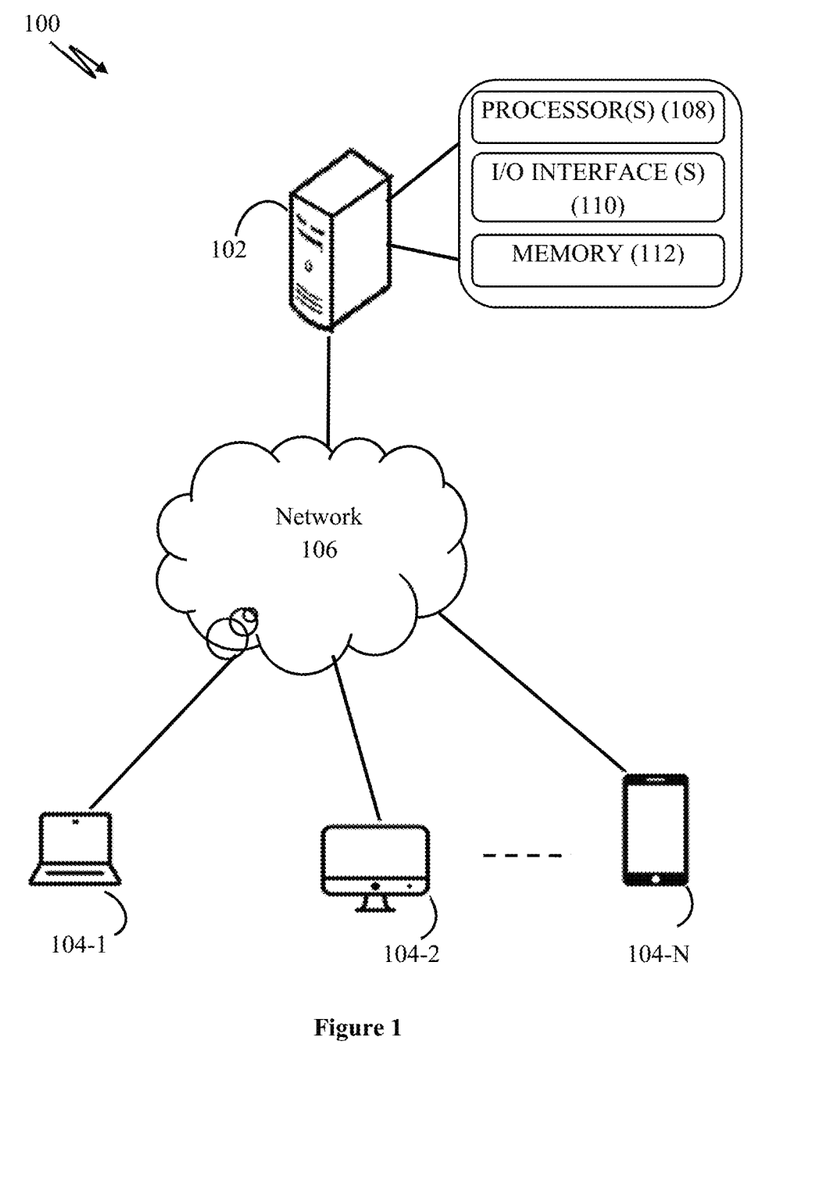
FIG. 1 illustrates a network implementation for analysing a fluid sample, in accordance with an embodiment of the present subject matter.

Referring now to FIG. 1, a network implementation 100 of a system 102 for analysing a fluid sample is disclosed. Initially, the system 102 receives an image of a test strip. In an example, the software may be installed on a user device 104-1. It may be noted that the one or more users may access the system 102 through one or more user devices 104-2, 104-3 . . . 104-N, collectively referred to as user devices 104, hereinafter, or applications residing on the user devices 104. The system 102 receives an image of a test strip from one or more user devices 104. Further, the system may also 102 receive a feedback from a user using the user devices 104.

Although the present disclosure is explained considering that the system 102 is implemented on a server, it may be understood that the system 102 may be implemented in a variety of computing systems, such as a laptop computer, a desktop computer, a notebook, a workstation, a virtual environment, a mainframe computer, a server, a network server, a cloud-based computing environment. It will be understood that the system 102 may be accessed by multiple users through one or more user devices 104-1, 104-2, 104-3, . . . 104-N. In one implementation, the system 102 may comprise the cloud-based computing environment in which the user may operate individual computing systems configured to execute remotely located applications. Examples of the user devices 104 may include, but are not limited to, a portable computer, a personal digital assistant, a handheld device, and a workstation. The user devices 104 are communicatively coupled to the system 102 through a network 106.

In one implementation, the network 106 may be a wireless network, a wired network, or a combination thereof. The network 106 can be implemented as one of the different types of networks, such as intranet, local area network (LAN), wide area network (WAN), the internet, and the like. The network 106 may either be a dedicated network or a shared network. The shared network represents an association of the different types of networks that use a variety of protocols, for example, Hypertext Transfer Protocol (HTTP), Transmission Control Protocol/Internet Protocol (TCP/IP), Wireless Application Protocol (WAP), and the like, to communicate with one another. Further, the network 106 may include a variety of network devices, including routers, bridges, servers, computing devices, storage devices, and the like.

In one embodiment, the system 102 may include at least one processor 108, an Input/Output (I/O) interface 110, and a memory 112. The at least one processor 108 may be implemented as one or more microprocessors, microcomputers, microcontrollers, digital signal processors, Central Processing Units (CPUs), state machines, logic circuitries, and/or any devices that manipulate signals based on operational instructions. Among other capabilities, the at least one processor 108 is configured to fetch and execute computer-readable instructions stored in the memory 112.

The I/O interface 110 may include a variety of software and hardware interfaces, for example, a web interface, a Graphical User Interface (GUI), and the like. The I/O interface 110 may allow the system 102 to interact with the user directly or through the client devices 104. Further, the I/O interface 110 may enable the system 102 to communicate with other computing devices, such as web servers and external data servers (not shown). The I/O interface 110 can facilitate multiple communications within a wide variety of networks and protocol types, including wired networks, for example, LAN, cable, etc., and wireless networks, such as Wireless Local Area Network (WLAN), cellular, or satellite. The I/O interface 110 may include one or more ports for connecting a number of devices to one another or to another server.

The memory 112 may include any computer-readable medium or computer program product known in the art, including, for example, volatile memory, such as static random access memory (SRAM) and dynamic random access memory (DRAM), and/or non-volatile memory, such as read only memory (ROM), erasable programmable ROM, flash memories, hard disks, Solid State Disks (SSD), optical disks, and magnetic tapes. The memory 112 may include routines, programs, objects, components, data structures, etc., which perform particular tasks or implement particular abstract data types. The memory 112 may include programs or coded instructions that supplement applications and functions of the system 102. In one embodiment, the memory 112, amongst other things, serves as a repository for storing data processed, received, and generated by one or more of the programs or the coded instructions.

As there are various challenges observed in the existing art, the challenges necessitate the need to build the system 102 for analysing a fluid sample. At first, a user may use the user device 104 to access the system 102 via the I/O interface 110. The user may register the user devices 104 using the I/O interface 110 in order to use the system 102. In one aspect, the user may access the I/O interface 110 of the system 102. The detail functioning of the system 102 is described below with the help of figures.

The present subject matter discloses a system 102 for analysing a fluid sample. The system receives an image of a test strip. It may be noted that a part of the test strip is dipped in a fluid sample. The fluid sample may be a biological fluid sample such as urine, saliva, blood, interstitial fluid or stool. The test strip may also be referred to as a dipstick or a urine test strip. The test strip is a basic diagnostic tool used to determine pathological changes in a patient's urine in standard urinalysis. In an embodiment, a user or a patient may click an image of the test strip using a smartphone. Further, the user may upload the image to the system. The image may comprise a dipped region and a non-dipped region. The dipped region may be the region of the test strip that is dipped in the urine sample or the fluid sample. The dipped region may comprise a set of chemical pads. The set of chemical pads may comprise one or more chemicals. The non-dipped region may comprise a set of colour markers, a set of position markers and a code. The set of colour markers may comprise one or more colour boxes having defined colour values.

Further to receiving the image, the system 102 may identify a set of regions in the image. The set of regions may comprise a code, a set of position markers, a set of colour markers, and a set of chemical pads. The set of chemical pads may comprise one or more chemicals depending on the test data. The set of chemical pads may also be referred as a set of reagent pads. The set of colour markers may comprise a plurality of boxes of defined colour values. The code may be a Quick Response (QR) code or a barcode printed on the test strip. The code comprises information related to a type of test being performed, chemical pad data, and details of the test strip, such as a lot number and manufacturing information. In an embodiment, the system may validate the image based on the set of regions.

In another embodiment, the test strip may be authenticated by scanning the code present on the test strip. The system may compare the lot number and the manufacturing information of the test strip with data stored in the memory 112 for the test strip. The system may validate the image of the test strip by scanning the code.

Further, the set of position markers may also be referred to as fiducial markers or fiducials. The set of position markers enables the system 102 for pose and orientation standardization. In other words, the system may accurately locate and measure the set of chemical pads and the set of colour markers on the test strip using the set of position markers. In an alternate embodiment, when the code is not present on the test strip, the set of position markers may be used to identify the type of test the user performs.

Further to identifying the set of regions, the system 102 may standardize the image using an alignment model and a lighting model. In order to standardize the image, the system 102 may detect a colour change of the test strip due to the fluid sample by analysing the set of colour markers and the set of chemical pads using the lighting model. Further, the system may detect the colour change of the test strip due to lighting conditions and camera features by analysing the set of colour markers using the lighting model. The lighting model may be a machine learning model trained to standardize the image by colour correction using a training dataset comprising a plurality of images of test strips captured using different types of cameras, and a corrected image for each of the plurality of images.

In an embodiment, the system may auto-calibrate the colour of the image by using the set of colour markers. The system may standardize the overexposed image of the test strip based on the set of colour markers.

Further, the system may adjust the colour values of the set of chemical pads based on the colour change due to the fluid sample, and due to lighting conditions and camera features. The system may adjust the colour values of the set of chemical pads based on a fluid colour prediction model.

In another embodiment, when the user clicks an image of the test strip using a smartphone, the image may get exposed to various environmental factors, such as lighting, shadows, and glare, which can affect colour matching. Additionally, different smartphone cameras have varying sensitivities to colours, resulting in differences in output between different cameras and smartphones. To address this issue, a set of colour markers is placed on the test strip. The set of colour markers enables the system to detect the deviation in colours caused due to imperfect lighting conditions when compared to a physical copy of the test strip.

In yet another embodiment, let us assume that the system receives a first image, of a test strip, captured from device A and a second image, of the same test strip, captured from the device B. The first image may be different from the second image because device A may have different white balance settings and different colour correction profiles than device B. The white balance settings may be associated with how devices (device A and device B) determine the white point for the image and if any tint should be applied to the other colours. The colour correction profile may be associated with how devices process colour saturation, black levels, highlights, and the contrast of colours in the image. In another example, first image may be different from second image because device A has different hardware (such as camera features comprising camera resolution, dimensions, filters, colour filters, lenses, crop factor, sensitivity, and so forth). In yet another example, the first image may be different from the second image because device A has different camera configuration or camera features (such as exposure time, shutter speed, aperture, ISO, and so forth).

In an embodiment, a user or a patient may click a tilted image of the test strip. Further, the system locates the set of position markers and standardizes the tilted image using the set of position markers. The system may use an alignment model to align the titled image of the test strip. In an example and not by way of any limitation, a perspective view or an isometric view of the image may be converted into a top view using the alignment model. The alignment model may be a machine learning model trained to convert a 3-Dimensional (3D) image into a standardized 2-Dimensional (2D) image using a training dataset comprising a plurality of 3D images of the test strip and a plurality of converted 2D images for the plurality of 3D images.

The set of colour markers present on the test strip enables the system to compensate for imperfect lighting conditions. The system detects the deviation in colours of the test strip caused by the lighting conditions by comparing the colour values of the test strip with the defined colour values of the set of colour markers. By doing so, the system may accurately determine the colours even if the lighting conditions are not ideal, leading to more reliable and accurate results. This can be especially useful in situations where the test is being performed in non-standard environments, such as at home or in a remote area with limited resources, where perfect lighting conditions cannot be ensured.

In an embodiment, the system may analyse the image to derive RGB (Red, Green, and Blue) colour values of the set of colour markers. Further, the RGB colour values may be converted into various colour spaces such as CIELab, HSB (Hue, Saturation, and Brightness) and HSL (Hue, Saturation, and Lightness).

The system uses CIELab colour space for detecting the change in the colour value. CIE L*a*b* (CIELab) is a colour space which is defined by the International Commission on Illumination (Commission internationale de l'éclairage, CIE). The colour values are expressed as three values: L* for perceptual lightness and a* and b* for the four unique colours of human vision: red, green, blue and yellow. The perceptual lightness value, L*, also referred to as "Lstar," defines black at 0 and white at 100. The a* axis is relative to the green-red opponent colours, with negative values toward green and positive values toward red. It may be noted that the a* axis defines the colour values between −128 to 128, wherein −128 refers to green and 128 refers to red. The b* axis represents the blue-yellow opponents, with negative numbers toward blue and positive toward yellow. It may be noted that the b* axis defines the colour values between −128 to 128, wherein −128 refers to blue and 128 refers to yellow. Unlike the Red, Green, Blue (RGB), and CMYK (Cyan, Magenta, Yellow, and Key) colour models, CIELAB is designed to approximate human vision. CIELab is helpful in predicting minor differences in colour.

Further to standardizing the image, the system 102 may obtain or fetch test data based on a code. The test data may comprise a set of health parameters and chemical pad data. The test data may be stored in at least one of the memory 112 and a user device 104. The set of health parameters may comprise a Potential of Hydrogen (pH) in urine, concentration of Glucose, Bilirubin, Ketone (Acetoacetic Acid), Blood, Protein, Urobilinogen, Leukocytes, Nitrites, Ascorbic Acid, and Specific Gravity. Further, the chemical pad data may comprise positions of the set of chemical pads, a list of chemicals in the set of chemical pads, and colour values of the set of chemical pads.

In an example and not by way of any limitation, the chemicals in the list of chemicals may comprise, but not limited to, Derivatized pyrrole amino acid ester, diazonium salt, buffer; p-arsanilic acid; N-(1-naphthyl) ethylenediamine; methyl red sodium salt; buffer and non-reactive ingredients. The set of chemicals may be different on the test strip based on the type of test being performed.

In an embodiment, the test data for "test strip A" may be fetched by the system when the user uploads the image of "test strip A" to the system. The test data may be different for different types of tests. In an embodiment, a number of health parameters that may be determined by the system depends on a number of chemical pads, from the set of chemical pads, present on the test strip. In an example and not by way of any limitation, a chemical pad may be used to determine one or more health parameters.

Further to obtaining the test data, the system 102 may determine a degree of chemical reaction by analysing the set of chemical pads based on the test data. In other words, the system may determine an extent of the chemical reaction by analysing the set of chemical pads based on the test data. The fluid sample causes the chemical reaction with the one or more chemicals of the set of chemical pads when the test strip is dipped in the fluid sample. The set of chemical pads may be analysed using a reaction model. The set of chemical pads may comprise one or more chemicals depending on the test data. Further, the extent of the chemical reaction may be determined based on a colour change in the set of chemical pads. The system may determine the colour change by comparing the colour values of the set of chemical pads in the image with the defined colour values of the set of chemical pads in the chemical pad data. Further, the extent of the chemical reaction is a percentage value between 0 and 100.

The reaction model is an image processing model trained to determine the extent of the chemical reaction using a training dataset comprising a plurality of images of test strips before being dipped in urine and after being dipped in the fluid sample, and a value for the extent of the chemical reaction for each of the plurality of images.

The below table shows the change in the colour values of the set of chemical pads:

| Chemicals | Pre-stored Colour Values | | | Colour Values After Dipping | | | The Extent of the chemical reaction |
|---|---|---|---|---|---|---|---|
| | L | a* | b* | L | a* | b* | |
| A | 10 | −100 | 10 | 15 | −90 | 20 | 40 |
| B | 30 | 10 | −60 | 33 | 15 | −50 | 15 |
| C | 80 | −90 | −10 | 80 | −90 | −1 | 5 |

The above table shows an example of a change in the colour of the set of chemical pads when the test strip is dipped in the urine. Similarly, the colour of other chemicals present on the test strip will also get affected when the set of chemical pads makes contact with the urine test strip. When the test strip is dipped into the urine or any fluid, the set of chemical pads absorbs the urine. Further, each pad from the set of chemical pads produces a different colour.

In an alternate embodiment, the system may generate an alert when the image is received after a predefined time is expired. In such instance, the fluid may react with the chemicals to a larger extent and the test results obtained may not be accurate. In an example, let us assume that a user uses a mobile application for urine analysis. The user opens the mobile application. The user is instructed to dip the test strip into a fluid sample. Further, the user is instructed to click an image of the test strip after a predefined time (e.g., 60 seconds to 120 seconds). As soon as the user dips the test strip, a timer is started on the mobile application so that the user can click the image at the right time. Once the timer ends, the user may upload the image of the test strip to the mobile application using the user device 104. It may be noted that the mobile application is installed in the user device. In an alternate embodiment, the user may click an image of the test strip from the mobile application installed on the user device 114. Further, the clicked image is sent to the system. In the example, when the user uploads the image after a defined time (e.g., after 150 seconds), the system may generate an alert indicating that the ideal time period or defined time period has lapsed. Additionally, the system may reject the images captured after the defined time period is expired.

Further to determining the extent of the chemical reaction, the system may compute the set of health parameters based on the extent of the chemical reaction. The set of health parameters may comprise a Potential of Hydrogen (pH) in urine, concentration of Glucose, Bilirubin, Ketone (Acetoacetic Acid), Blood, Protein, Urobilinogen, Leukocytes, Nitrites, Ascorbic Acid, and Specific Gravity. The set of health parameters is computed using a test model.

The test model is a machine learning model trained to compute a value of a health parameter. The machine learning model is trained using a training dataset including a list of chemicals, a plurality of extents of chemical reactions for the list of chemicals, and corresponding values of health parameters for the list of chemicals. The test model is continuously trained as and when new training data is available. In an embodiment, when the system computes the set of health parameters, the urine analysis data is fed back to the test model. Thus, the test model is retrained when the user performs a urine test over a period of time.

The test model is trained by following below steps:

Initially, a large number of images of test strips are collected. Further, each image is labelled with a value of a health parameter of the set of health parameters. Further, the images are pre-processed to ensure that the images are all of the same sizes, have the same orientation, and are free of any artifacts or noise that could interfere with the analysis. The pre-processing techniques may comprise normalization, resizing, and denoising. During pre-processing, correction for all external lighting and phone colour correction are also considered.

Further to pre-processing, one or more features are extracted from each image to train the test model. For example, the colour values of each pixel in the image are extracted, and edge detection and texture analysis are used to extract more complex features, and alike.

Further, the extracted features are used to train the machine learning-based test model. The machine learning models may comprise convolutional neural networks (CNNs), support vector machines (SVMs), and decision trees.

In an embodiment, the system may also comprise a database comprising data related to a set of chemical pads and the extent of the chemical reaction when the set of chemical pads is dipped in the urine. The database may be stored in the memory 112. Further, the database may include the corresponding value of the health parameter against different extents of the chemical reaction. In other words, the system comprises a prestored database of the extent of chemical reaction for each chemical and the corresponding value of the health parameter. For example, an extent of the chemical reaction of chemical A is 80. Thus, the system may determine the protein (health parameter) value of 15 mg/dL. Similarly, when the extent of the chemical reaction of chemical B is 70, the system may determine the pH is 7.5.

Figure 7:
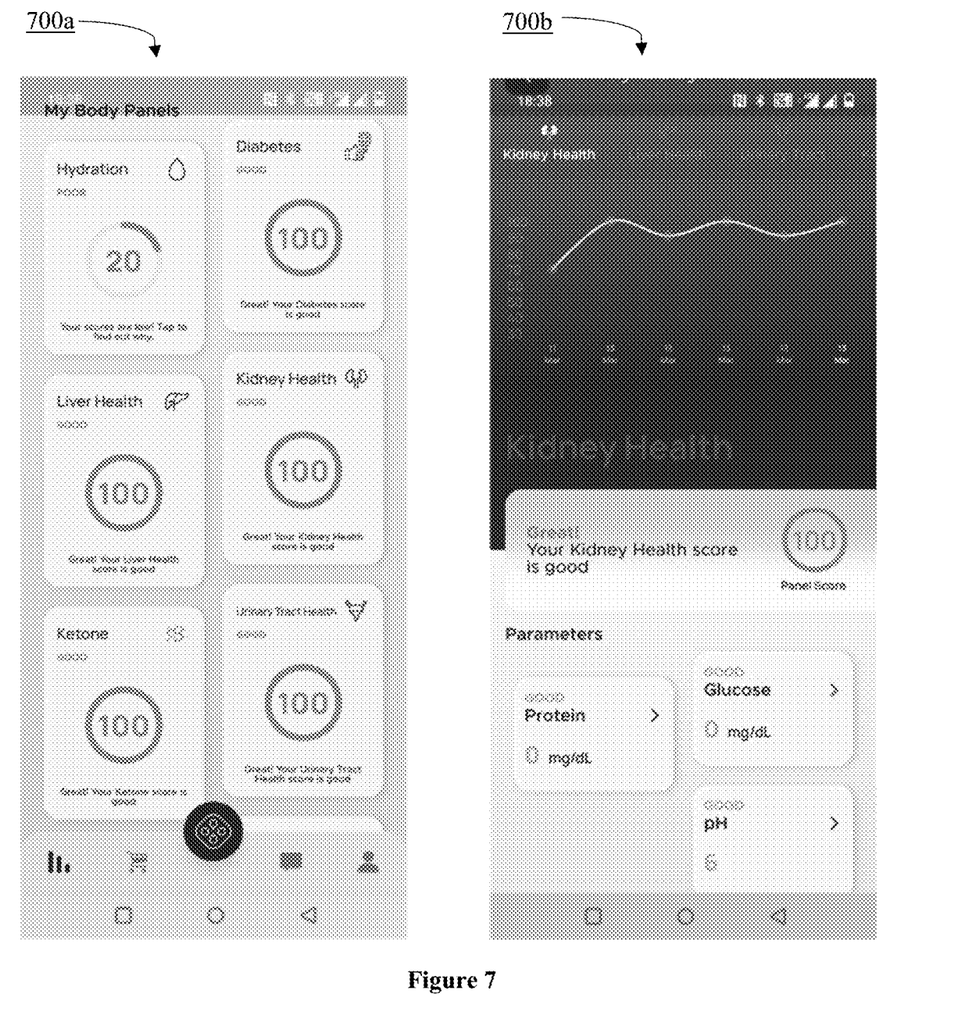
FIG. 7 illustrates an example of a Graphical User Interface (GUI) depicting a health report obtained after the fluid sample analysis, in accordance with an embodiment of the present subject matter.
Figure 8:
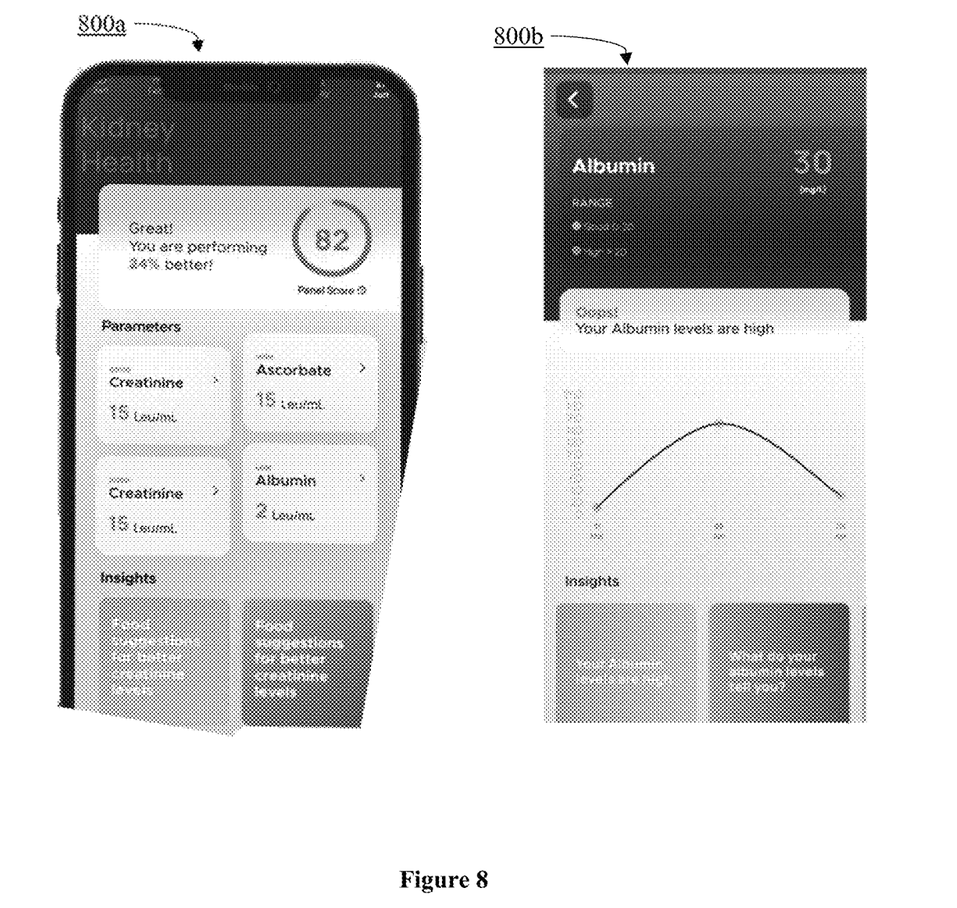
FIG. 8 illustrates an example of a Graphical User Interface (GUI) depicting recommendations provided by the system to improve a set of health parameters, in accordance with an embodiment of the present subject matter.

In an embodiment, the system may display the set of health parameters, a time of the test taken, and a status of the test via a graphical user interface of a user device. FIG. 7 illustrates an example of the health report 700a and 700b. The figure shows a set of health parameters comprising kidney health, liver health, hydration, urinary tract infection, pH, and ketones. Similarly, the remaining set of health parameters is also displayed to the user. In an embodiment, the user may download a urinalysis report from the GUI. In another embodiment, the system may provide recommendations to improve a set of health parameters. FIG. 8 shows examples (800a and 800b) of the recommendation or suggestion provided by the system 102. Example 800a illustrates that the system is suggesting food to get the better creatine levels. Example 800b shows that the health parameter e.g., Albumin is high. Further, the system suggests or recommends some articles or reading material that can help the user to better understand the problem and the solution for the problem.

In an example and not by way of any limitation, the set of chemical pads may also comprise an empty pad specifically for predicting the colour of the fluid or the urine. When the test strip is dipped in the fluid, the empty pad absorbs the fluid and maintains the colour of the fluid. When the system receives an image of the test strip, the system initially determines whether a white colour between the set of position markers is the same as the colour of the empty pad. When there is a difference between the lighting conditions of the white colour between the set of position markers and the colour of the empty pad, the system may apply a white balancing algorithm (histogram equalization) to make the image lighting uniform. Further, the system may determine the colour value of the empty pad. The empty pad may be either white, grey, or not white. The colour value is then compared with the prestored colour value of the urine to predict the colour of the fluid sample of the user using a fluid colour prediction model.

In an example, a user can analyse the fluid sample in two steps comprising:

Step 1: Upload an image of the test strip after dipping the test strip into a fluid sample after a predefined time (e.g., 60 seconds to 120 seconds).

Step 2: Receive a urine analysis report in real-time. The report comprises the value of the set of health parameters.

In an embodiment, a number of chemicals may be increased in the set of chemical pads in order to determine more health parameters of the user.

In an alternate embodiment, the user may click an image of the test strip using a user device. Further, the user device may identify a set of regions in the image. The set of regions comprises a code, a set of position markers, a set of colour markers, and a set of chemical pads. Subsequently, the user device may determine test data based on the code. The test data may be prestored on the user device. The test data comprises a set of health parameters, and chemical pad data. Further, the user device may determine a degree of chemical reaction by analysing the set of chemical pads based on the test data. The set of chemical pads is analysed using a reaction model. Further, the user device may display the set of health parameters based on the extent of the chemical reaction. The set of health parameters is computed using a test model.

Figure 2:
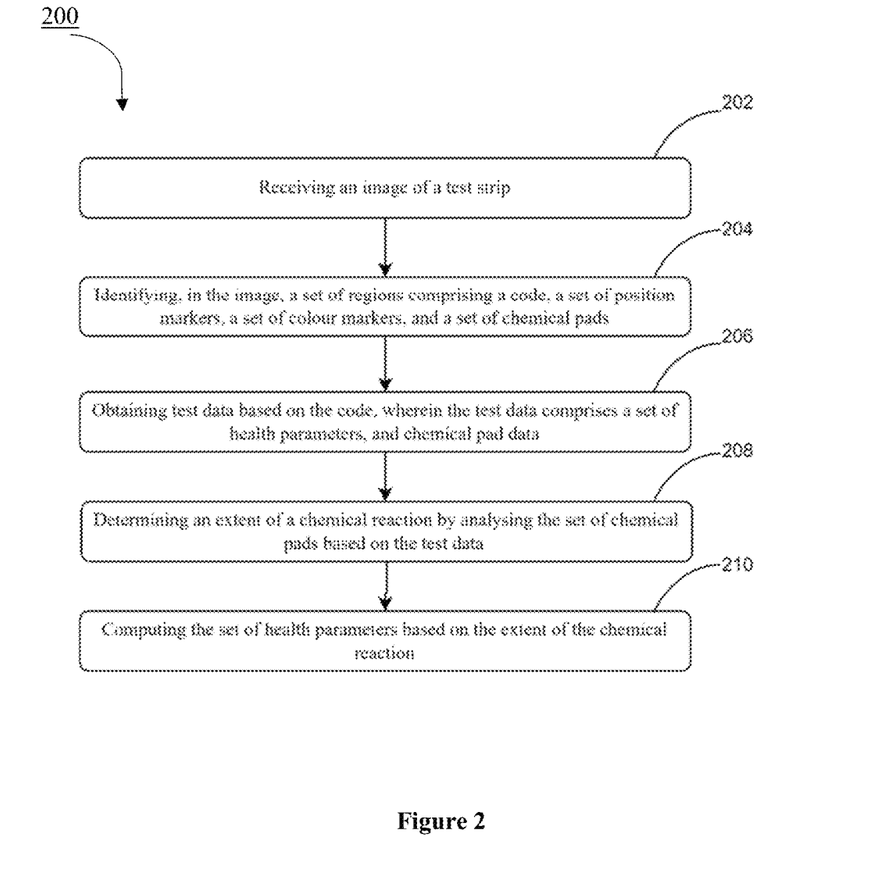
FIG. 2 illustrates a method for analysing a fluid sample, in accordance with an embodiment of the present subject matter.

Referring now to FIG. 2, a method 200 for analysing a fluid sample is shown, in accordance with an embodiment of the present subject matter. The method 200 may be described in the general context of computer-executable instructions. Generally, computer-executable instructions can include routines, programs, objects, components, data structures, procedures, modules, functions, etc., that perform particular functions or implement particular abstract data types.

The order in which the method 200 is described is not intended to be construed as a limitation, and any number of the described method blocks can be combined in any order to implement the method 200 or alternate methods for analysing a fluid sample. Additionally, individual blocks may be deleted from the method 200 without departing from the scope of the subject matter described herein. Furthermore, the method 200 for analysing a fluid sample can be implemented in any suitable hardware, software, firmware, or combination thereof. However, for ease of explanation, in the embodiments described below, the method 200 may be considered to be implemented in the above-described system 102.

At block 202, an image of a test strip may be received. It may be noted that a part of the test strip is dipped in a fluid sample.

At block 204, a set of regions in the image may be identified. The set of regions comprises a code, a set of position markers, a set of colour markers, and a set of chemical pads.

At block 206, test data may be obtained based on the code. The test data comprises a set of health parameters, and chemical pad data.

At block 208, a degree of chemical reaction may be determined by analysing the set of chemical pads based on the test data. The set of chemical pads is analysed using a reaction model.

At block 210, the set of health parameters may be computed based on the extent of the chemical reaction. The set of health parameters is computed using a test model.

Figure 6:
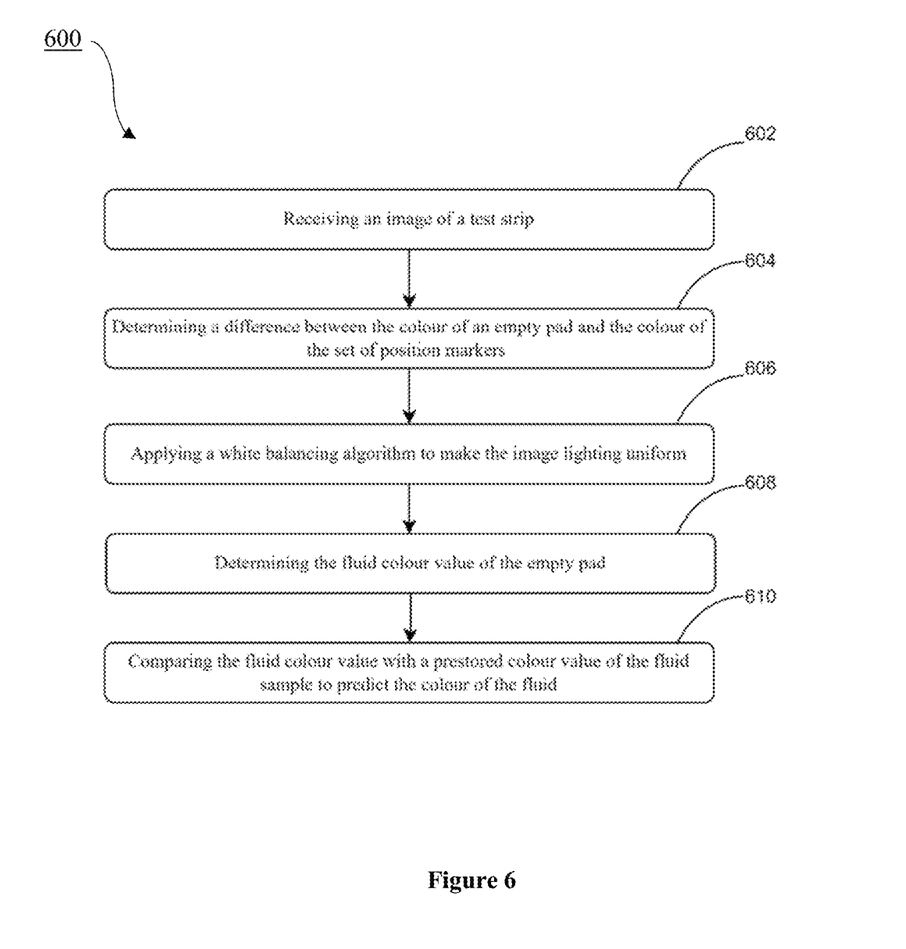
FIG. 6 illustrates a method for predicting a colour of the fluid sample, in accordance with an embodiment of the present subject matter.

Referring now to FIG. 6, a method 600 for predicting a colour of the fluid sample is shown, in accordance with an embodiment of the present subject matter. The method 600 may be described in the general context of computer-executable instructions. Generally, computer-executable instructions can include routines, programs, objects, components, data structures, procedures, modules, functions, etc., that perform particular functions or implement particular abstract data types.

The order in which the method 600 is described is not intended to be construed as a limitation, and any number of the described method blocks can be combined in any order to implement the method 600 or alternate methods for predicting the colour of the fluid sample. Additionally, individual blocks may be deleted from the method 600 without departing from the scope of the subject matter described herein. Furthermore, the method 600 for predicting the colour of the fluid sample can be implemented in any suitable hardware, software, firmware, or combination thereof. However, for ease of explanation, in the embodiments described below, the method 600 may be considered to be implemented in the above-described system 102.

At block 602, an image of a test strip may be received. It may be noted that a part of the test strip is dipped in a fluid sample. The fluid sample may be a biological fluid sample such as urine, saliva, blood, interstitial fluid or stool.

At block 604, a difference between the colour of the empty pad and the colour between the set of position markers may be determined.

At block 606, a white balancing algorithm may be applied in order to make the image lighting uniform.

At block 608, the urine colour value of the empty pad may be determined. In an example and not by way of any limitation, the system may derive the RGB colour values of the empty pad. Further, the RGB colour values may be converted into CIELab colour space.

At block 610, the urine colour value may be compared with a prestored colour value of the fluid sample to predict the colour of the urine. In an example, the system may display the colour of the urine to the user. In an embodiment, the system may track the colour of the fluid sample over a period of time.

Figure 3:
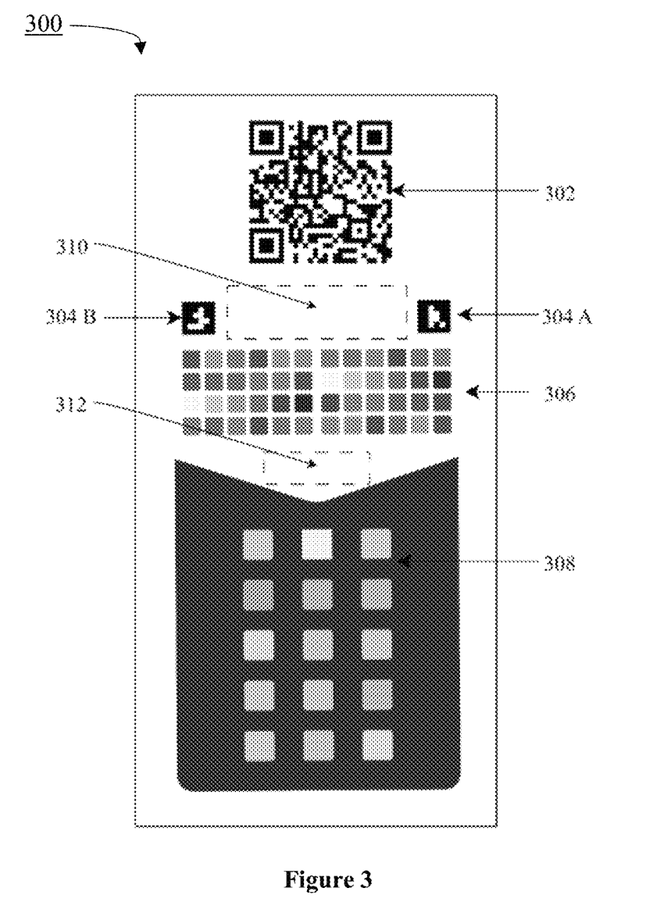
FIG. 3 illustrates an example of the test strip, in accordance with an embodiment of the present subject matter.

Referring now to FIG. 3, an example of the test strip 300 is illustrated. The test strip 300 comprises a set of regions (302, 304 A, 304 B, 306, 308). The set of regions (302, 304 A, 304 B, 306, 308) comprises a code 302, a set of position markers 304 A and 304 B, a set of colour markers 306, and a set of chemical pads 308. The code 302 comprises information related to a type of test being performed and details of the test strip 300, such as lot number, and manufacturing information. In an embodiment, the system 102 may validate an image of the test strip 300 based on the set of regions (302, 304 A, 304 B, 306, 308). The set of position markers 304 A and 304 B helps the system 102 with pose and orientation standardization. Further, the set of colour markers 306 is placed to ensure that there is no loss of information in the image of the test strip 300 when compared to a physical copy of the test strip 300. Furthermore, the set of chemical pads 308 may comprise one or more chemicals. It may be noted that the user dips the test strip 300 in the urine. The set of chemical pads 308 reacts with the fluid sample. Further, an area 310 between the set of position markers is shown. The area has a white colour. Further, a band 312, coloured in white, is an upper region of the set of chemical pads. When the test strip 300 is dipped in the fluid sample the set of chemical pads and the band may come in contact with the fluid sample. Further, the colour of the band may change due to the urine. The system may compare the colour of the area 310 and the colour of the band 312 to determine whether the urine is dipped in urine or not.

Figure 4:
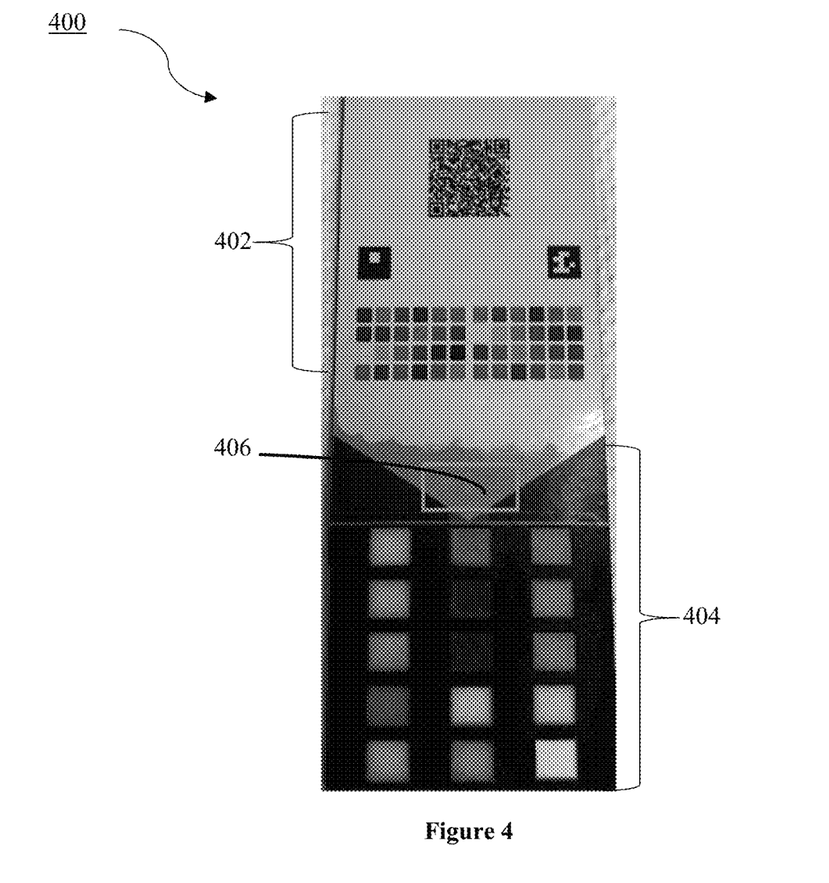
FIG. 4 illustrates an example of an image of the test strip dipped in a fluid sample, in accordance with an embodiment of the present subject matter.

Referring now to FIG. 4, an example of the image of the test strip 400 dipped in a fluid sample is illustrated. The image of the test strip 400 comprises a dipped region 402 and a non-dipped region 404. Further, the band 406 shows an upper region of the set of chemical pads. The band is also dipped in the fluid sample.

In an embodiment, the system 102 may determine an elapsed time based on a colour change of the dipped region 402 using a machine learning model referred to as a chroma-net model. The elapsed time may be a time duration between dipping of the test strip 400 in the fluid sample and clicking the image. In an embodiment, the machine learning model may be trained using a training dataset of a set of images of a plurality of test strips dipped in a fluid sample. The set of images comprises one or more images of the plurality of test strips, and wherein the one or more images are clicked at one or more predetermined elapsed times. Consider an example for a test strip used to perform a Urinary Tract Infection (UTI) test by dipping the test strip in a urine sample.

The chroma-net model may be trained using one or more images of the test strip dipped in the urine sample. The one or more images may comprise a plurality of images clicked 0 seconds after the test strip is dipped in the urine sample, a plurality of images clicked 30 seconds after the test strip is dipped in the urine sample, a plurality of images clicked 60 seconds, 90 seconds, 120 seconds, 150 seconds, and 180 seconds after the test strip is dipped in the urine sample. Each of the one or more images may be annotated with the corresponding elapsed time. Further, the chroma-net model may be trained to detect a colour change between two images using a training dataset comprising a plurality of images of dipped test strips, a plurality of images of non-dipped test strips, and a corresponding colour change value for a pair of images comprising an image from the plurality of dipped strips and an image from a plurality of non-dipped test strips. The pair of images comprises images of test strips for a common test.

The system may use the chroma-net model to determine the elapsed time for the received image by comparing the received image with the plurality of images in the training dataset of the chroma-net model. The system may identify an image, from the training dataset, similar to the received image. Further, the system may obtain the elapsed time of the similar image from the training dataset to determine the elapsed time for the received image based on the chroma-net model.

Further to determining the elapsed time for the received image, the system may compare the elapsed time with the ideal time. The ideal time may be based on the code present in the non-dipped region. The ideal time may be different for different type of tests. The ideal time corresponds to the duration between dipping a test strip in a fluid sample and clicking an image of the test strip after dipping it. The time duration for the ideal time may be enough for the chemicals on the chemical pads to react with compounds in the fluid sample completely. Finally, the system may compute a validity score based on comparing the elapsed time with the ideal time. The validity score may be indicated by a value between 0 and 100. The validity score may be inversely proportional to an absolute value of the difference between the elapsed time and the ideal time. The validity score may be computed using a pre-stored database of elapsed time, the difference between an elapsed time and ideal time, corresponding validity scores, and at least one of the matching, sorting, and searching algorithms.

In an embodiment, the system may generate a feedback for a user to click a new image based on the validity score. In case the validity score is less than a threshold, the system may request the user to click a new image and upload the new image as the received image to the system.

For example, let us assume that the threshold for the validity score is 60, the ideal time is 60 seconds and the determined elapsed time of the received image in the example is 120 seconds. The validity score of the image is 20. The system will generate a feedback for the user to click a new image.

Consider another example, let us assume that the threshold for the validity score is 60, the ideal time is 60 seconds and the determined elapsed time of the received image in the example is 20 seconds. The validity score of the image is 30. The system will generate a feedback for the user to click a new image.

Consider another example, let us assume that the threshold for the validity score is 60, the ideal time is 60 seconds and the determined elapsed time of the received image in the example is 60 seconds. The validity score of the image is 100. The system will not generate a feedback.

In case the validity score is greater than the threshold, the system may validate the received image for a medical test. The medical test may be performed by analysing the received image using one or more machine learning algorithms to determine the set of health parameters.

Figure 5:
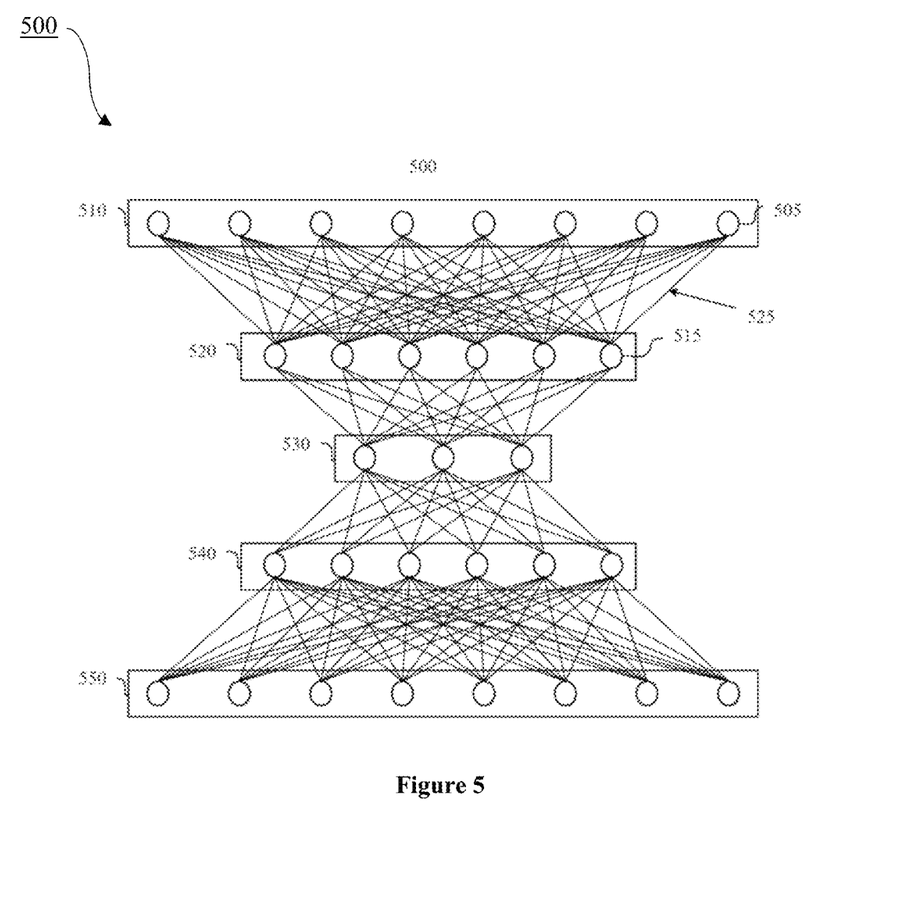
FIG. 5 illustrates an example artificial neural network, in accordance with an embodiment of the present subject matter.

FIG. 5 illustrates an example artificial neural network ("ANN") 500 used to train at least one of the machine learning models including the lighting model, alignment model, test model, and other image processing models implemented in the system. In particular embodiments, an ANN may refer to a computational model comprising one or more nodes. Example ANN 500 may comprise an input layer 510, hidden layers 520, 530, 540, and an output layer 550. Each layer of the ANN 500 may comprise one or more nodes, such as a node 505 or a node 515. In particular embodiments, each node of an ANN may be connected to another node of the ANN. As an example and not by way of limitation, each node of the input layer 510 may be connected to one of more nodes of the hidden layer 520. In particular embodiments, one or more nodes may be a bias node (e.g., a node in a layer that is not connected to and does not receive input from any node in a previous layer). In particular embodiments, each node in each layer may be connected to one or more nodes of a previous or subsequent layer. Although FIG. 5 depicts a particular ANN with a particular number of layers, a particular number of nodes, and particular connections between nodes, this disclosure contemplates any suitable ANN with any suitable number of layers, any suitable number of nodes, and any suitable connections between nodes. As an example and not by way of limitation, although FIG. 5 depicts a connection between each node of the input layer 510 and each node of the hidden layer 520, one or more nodes of the input layer 510 may not be connected to one or more nodes of the hidden layer 520.

In particular embodiments, an ANN may be a feedforward ANN (e.g., an ANN with no cycles or loops where communication between nodes flows in one direction beginning with the input layer and proceeding to successive layers). As an example and not by way of limitation, the input to each node of the hidden layer 520 may comprise the output of one or more nodes of the input layer 510. As another example and not by way of limitation, the input to each node of the output layer 550 may comprise the output of one or more nodes of the hidden layer 540. In particular embodiments, an ANN may be a deep neural network (e.g., a neural network comprising at least two hidden layers). In particular embodiments, an ANN may be a deep residual network. A deep residual network may be a feedforward ANN comprising hidden layers organized into residual blocks. The input into each residual block after the first residual block may be a function of the output of the previous residual block and the input of the previous residual block. As an example and not by way of limitation, the input into residual block N may be $F(x)+x$, where $F(x)$ may be the output of residual block N−1, x may be the input into residual block N−1. Although this disclosure describes a particular ANN, this disclosure contemplates any suitable ANN.

In particular embodiments, an activation function may correspond to each node of an ANN. An activation function of a node may define the output of a node for a given input. In particular embodiments, an input to a node may comprise a set of inputs. As an example and not by way of limitation, an activation function may be an identity function, a binary step function, a logistic function, or any other suitable function.

In particular embodiments, the input of an activation function corresponding to a node may be weighted. Each node may generate output using a corresponding activation function based on weighted inputs. In particular embodiments, each connection between nodes may be associated with a weight. As an example and not by way of limitation, a connection 525 between the node 505 and the node 515 may have a weighting coefficient of 0.4, which may indicate that 0.4 multiplied by the output of the node 505 is used as an input to the node 515. In particular embodiments, the input to nodes of the input layer may be based on a vector representing an object. Although this disclosure describes particular inputs to and outputs of nodes, this disclosure contemplates any suitable inputs to and outputs of nodes. Moreover, although this disclosure may describe particular connections and weights between nodes, this disclosure contemplates any suitable connections and weights between nodes.

In particular embodiments, the ANN may be trained using training data. As an example and not by way of limitation, training data may comprise inputs to the ANN 500 and an expected output. As another example and not by way of limitation, training data may comprise vectors each representing a training object and an expected label for each training object. In particular embodiments, training the ANN may comprise modifying the weights associated with the connections between nodes of the ANN by optimizing an objective function. As an example and not by way of limitation, a training method may be used (e.g., the conjugate gradient method, the gradient descent method, the stochastic gradient descent) to backpropagate the sum-of-squares error measured as a distances between each vector representing a training object (e.g., using a cost function that minimizes the sum-of-squares error). In particular embodiments, the ANN may be trained using a dropout technique. As an example and not by way of limitation, one or more nodes may be temporarily omitted (e.g., receive no input and generate no output) while training. For each training object, one or more nodes of the ANN may have some probability of being omitted. The nodes that are omitted for a particular training object may be different than the nodes omitted for other training objects (e.g., the nodes may be temporarily omitted on an object-by-object basis). Although this disclosure describes training the ANN in a particular manner, this disclosure contemplates training the ANN in any suitable manner.

Exemplary embodiments discussed above may provide certain advantages. Though not required to practice aspects of the disclosure, these advantages may include those provided by the following features.

The system and the method enable image processing and machine learning algorithms to provide a more accurate and reliable method for analysing fluid samples compared to the traditional manual interpretation of test strips, which is subjective and prone to human error.

The system and the method enable automated analysis of fluid samples.

The system and the method enable a smartphone camera as the image-capturing device by eliminating the need for expensive and dedicated hardware such as pre-calibrated scanners, making the system more cost-effective and accessible.

The system is easy to use, as the patient or user only needs to take a picture of the test strip using their smartphone and upload it to the system for analysis. The system's algorithms automatically create a urine analysis report.

The system and the method enable real-time urine test results, which can help to improve patient outcomes by allowing for faster diagnosis and treatment.

The test model used to compute the set of health parameters is continuously updated and trained over time as more data is collected, leading to improved accuracy and reliability of the results.

Although implementations for methods and system for analysing a fluid sample have been described in language specific to structural features and/or methods, it is to be understood that the appended claims are not necessarily limited to the specific features or methods described. Rather, the specific features and methods are disclosed as examples of implementations for analysing a fluid sample.

The invention claimed is:

1. A method for analysing a fluid sample, wherein the method comprises:
    receiving, by a processor, an image of a test strip dipped in the fluid sample;
    identifying, by the processor, a set of regions in the image, wherein the set of regions comprises a code, a set of position markers, a set of colour markers, and a set of chemical pads;
    obtaining, by the processor, test data based on the code, wherein the test data comprises a set of health parameters and chemical pad data;
    determining, by the processor, an extent of chemical reaction by analysing the set of chemical pads based on the test data, wherein the set of chemical pads is analysed using a reaction model; and
    computing, by the processor, respective values of each of the health parameter in the set of health parameters based on the extent of the chemical reaction, wherein the set of health parameters is computed using a test model, wherein the test model is a machine learning model trained to compute a value of a health parameter using a training dataset of a list of chemicals, extent of chemical reactions for the list of chemicals, and corresponding values of health parameters for the list of chemicals.

2. The method as claimed in claim 1, wherein the set of chemical pads comprises one or more chemicals depending on the test data.

3. The method as claimed in claim 2, wherein the fluid sample causes the chemical reaction with the one or more chemicals of the set of chemical pads when the test strip is dipped in the fluid sample.

4. The method as claimed in claim 1, wherein the set of colour markers comprises a plurality of boxes of defined colour values.

5. The method as claimed in claim 1, wherein the set of health parameters comprises a Potential of Hydrogen (pH) of the fluid sample, concentration of Glucose, Bilirubin, Ketone (Acetoacetic Acid), Blood, Protein, Urobilinogen, Leukocytes, Nitrites, and Ascorbic Acid, and Specific Gravity.

6. The method as claimed in claim 1, wherein the chemical pad data comprises position of the set of chemical pads and the list of chemicals in the set of chemical pads.

7. The method as claimed in claim 1, wherein the extent of the chemical reaction is determined based on a colour change of the set of chemical pads, and wherein the colour change is determined by comparing colour values of the set of chemical pads in the image with colour values of the set of chemical pads in the chemical pad data.

8. The method as claimed in claim 1, wherein the extent of the chemical reaction is a percentage value between 0 and 100.

9. The method as claimed in claim 1, further comprises standardizing the image using at least one of an alignment model and a lighting model.

10. The method as claimed in claim 9, wherein the alignment model is a machine learning model trained to convert a 3-Dimensional (3D) image into a standardized 2-Dimensional (2D) image.

11. The method as claimed in claim 9, wherein the lighting model is a machine learning model trained to standardize the image to compensate the imperfect lighting conditions.

12. The method as claimed in claim 1, wherein the reaction model is a machine learning model trained to determine the extent of the chemical reaction using a training dataset comprising a plurality of images of test strips before being dipped in the fluid sample and after being dipped in the fluid sample, and a value for the extent of the chemical reaction for each of the plurality of images.

13. The method as claimed in claim 1, further comprises generating an alert when the image is received after a predefined time is expired.

14. The method as claimed in claim 1, further comprises validating the image based on the set of regions.

15. The method as claimed in claim 9, wherein standardizing the image comprises:
- detecting a colour change of the test strip by analysing the set of colour markers and the set of chemical pads using the lighting model;
- detecting the colour change of the test strip due to lighting conditions and camera features by analysing the set of colour markers using the lighting model; and
- adjusting colour values of the set of chemical pads based on the colour change due to the fluid sample, and lighting conditions and camera features.

16. The method as claimed in claim 1, wherein the fluid sample comprises one of urine, saliva, blood, interstitial fluid and stool.

17. A system for analysing a fluid sample, wherein the system comprises:
- a memory; and
- a processor coupled to the memory, wherein the processor is configured to execute program instructions stored in the memory for:
  - receiving an image of a test strip dipped in the fluid sample;
  - identifying a set of regions in the image, wherein the set of regions comprises a code, a set of position markers, a set of colour markers, and a set of chemical pads;
  - obtaining test data based on the code, wherein the test data comprises a set of health parameters and chemical pad data;
  - determining an extent of chemical reaction by analysing the set of chemical pads based on the test data, wherein the set of chemical pads is analysed using a reaction model; and
  - computing respective values of each of the health parameter in the set of health parameters based on the extent of the chemical reaction, wherein the set of health parameters is computed using a test model, wherein the test model is a machine learning model trained to compute a value of a health parameter using a training dataset of a list of chemicals, extent of chemical reactions for the list of chemicals, and corresponding values of health parameters for the list of chemicals.

18. A non-transitory computer program product having embodied thereon a computer program for analysing a fluid sample, the computer program product storing instructions for:
- receiving an image of a test strip dipped in the fluid sample;
- identifying a set of regions in the image, wherein the set of regions comprises a code, a set of position markers, a set of colour markers, and a set of chemical pads;
- obtaining test data based on the code, wherein the test data comprises a set of health parameters and chemical pad data;
- determining an extent of chemical reaction by analysing the set of chemical pads based on the test data, wherein the set of chemical pads is analysed using a reaction model; and
- computing respective values of each of the health parameter in the set of health parameters based on the extent of the chemical reaction, wherein the set of health parameters is computed using a test model, wherein the test model is a machine learning model trained to compute a value of a health parameter using a training dataset of a list of chemicals, extent of chemical reactions for the list of chemicals, and corresponding values of health parameters for the list of chemicals.

* * * * *